United States Patent [19]

Kubo et al.

[11] Patent Number: 4,548,811
[45] Date of Patent: * Oct. 22, 1985

[54] WAVING LOTION FOR COLD WAVING

[75] Inventors: Sanae Kubo, Sagamihara; Fumiaki Nakamura, Yokohama, both of Japan

[73] Assignee: Shiseido Company Ltd., Tokyo, Japan

[*] Notice: The portion of the term of this patent subsequent to Oct. 15, 2002 has been disclaimed.

[21] Appl. No.: 545,817

[22] Filed: Oct. 27, 1983

[30] Foreign Application Priority Data

Nov. 8, 1982 [JP] Japan ................ 57-195798

[51] Int. Cl.⁴ .................... A61K 7/09; A61K 7/11; A61L 13/00
[52] U.S. Cl. .................................. 424/71; 424/72; 424/76
[58] Field of Search ...................... 424/71, 72, 76

[56] References Cited

U.S. PATENT DOCUMENTS

| 4,024,223 | 5/1977 | Noda et al. | 424/235 |
| 4,030,512 | 6/1977 | Papantoniou et al. | 424/71 |
| 4,041,150 | 8/1977 | Karjala | 424/DIG. 2 |
| 4,267,166 | 5/1981 | Yajima | 424/76 |
| 4,358,286 | 11/1982 | Grollier et al. | 424/74 |

FOREIGN PATENT DOCUMENTS 521369  7/1953  France ................ 424/71

OTHER PUBLICATIONS

Asama, Chem. Abst. Reg. No. 98:124514p.
Yajima, Chem. Abst. Reg. No. 94:36133a.

Primary Examiner—Albert T. Meyers
Assistant Examiner—Freda Abramson
Attorney, Agent, or Firm—Sprung, Horn, Kramer & Woods

[57] ABSTRACT

A waving lotion for cold waving comprising:
(i) a mercapto compound and (ii) an aqueous mixture obtained by heating (a) at least one compound selected from the group consisting of the compounds having the general formulae (I) to (XX),

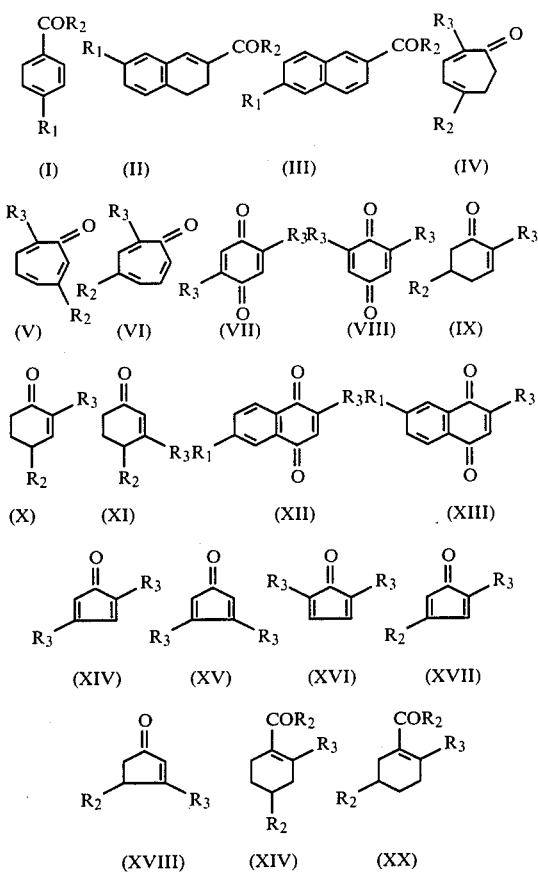

wherein $R_1$ is hydrogen or an electron attractive group, $R_2$ is hydrogen or an alkyl group having 1 to 4 carbon atoms, and $R_3$ is hydrogen, a hydroxyl group, or a methyl group and (b) at least one cyclodextrin selected from the group consisting of $\alpha$, $\beta$, $\gamma$, and $\delta$-cyclodextrins in an aqueous phase at a mole ratio of (a):(b)=1:9—1:1 at a temperature of 50° C. to 100° C.

This waving lotion has no substantial mercaptan odor and generates no substantial or less of a mercaptan odor when applied to the hair.

4 Claims, No Drawings

WAVING LOTION FOR COLD WAVING

BACKGROUND OF THE INVENTION

1. Field of the Invention

The present invention relates to a waving lotion for cold waving. More specifically, it relates to a waving lotion for cold waving having no substantial mercaptan odor and generating no substantial or less of a mercaptan odor when applied to the hair, which is formulated by incorporating a heat treated aqueous mixture of (a) p-diacetylbenzene, methyl-β-naphtyl ketone, or a similar compound and (b) a cyclodextrin into a conventional waving lotion.

2. Description of the Prior Art

As is well known in the art, permanent waving lotions are composed of (i) waving lotions containing, as a main component, reducing agents, that is, mercapto compounds such as thioglycolic acid and cysteine and (ii) neutralizers containing oxidizing agents such as sodium bromate and hydrogen peroxide. However, the use of conventional waving lotions involves problems in that conventional waving lotions per se have a specific mercaptan odor and in that conventional waving lotions generates a large amount of mercaptan having an extremely unpleasant odor when applied to the hair. Thus, the use of conventional waving lotions is not desirable for consumers and beauticians from the viewpoints of environmental health.

Various attempt have been made to eliminate the above-mentioned unpleasant odor. Typical conventional methods for eliminating the unpleasant mercaptan odor are so-called masking methods in which perfumes having a strong odor are incorporated into waving lotions to thereby sensuously mask the unpleasant mercaptan odor. However, the amount of mercaptan generated during the application processing of waving lotions to the hair is very large and mercaptan odor is typical bad or unpleasant odor regulated as a polluting odor. Accordingly, mercaptan odor included in, for example, the entire space of beauty salons cannot be completely masked by perfume-utilizing masking methods. On the other hand, some people dislike the perfumes having strong odor generally used in the masking methods due to their strong and heavy odor.

For the above-mentioned reasons, it is considered that the mercaptan odor per se must be eliminated from waving lotions in order to fundamentally solve the above-mentioned problems of unpleasant odor. However, in order to solve the above-mentioned problems, if deodorants capable of suppressing the vaporization of mercaptans through chemical reactions are incorporated into waving lotions, or if deodorants are separately applied to the hair simultaneous with the application of waving lotions, mercaptans such as thioglycolic acid and cysteine contained as a main component in waving lotions are reacted with the deodorants to inhibit the desirable reducing effect essential for waving lotions and, therefore, the waving effect or power of waving lotions is disadvantageously decreased. Furthermore, after the deodorants are consumed, undesirable mercaptans are again generated.

SUMMARY OF THE INVENTION

Accordingly, the object of the present invention is to fundamentally eliminate the above-mentioned generation of an unpleasant odor from waving lotions and to provide a waving lotion having no substantial mercaptan odor and generating no substantial or less of a mercaptan odor when applied to the hair.

Other objects and advantages of the present invention will be apparent from the following description.

In accordance with the present invention, there is provided a waving lotion for cold waving comprising: (i) a mercapto compound and (ii) an aqueous mixture obtained by heating (a) at least one compound selected from the group consisting of the compounds having the general formulae (I) to (XX),

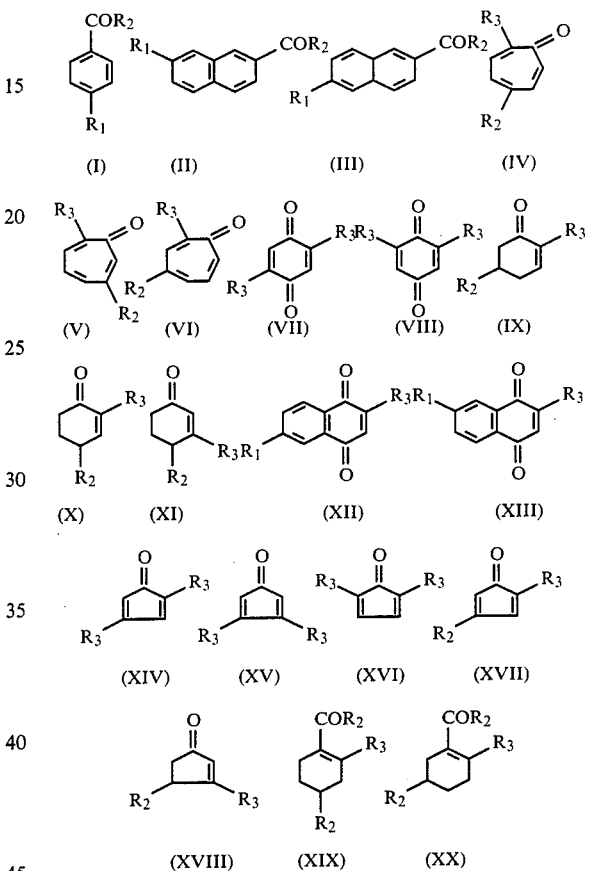

wherein $R_1$ is hydrogen or an electron attractive group such as $COCH_3$, $COC_2H_5$, $COC_3H_7$, $OCOCH_3$, $OCOC_2H_5$, $OCOC_3H_7$, Cl, Br, I, $SCOCH_3$, SCN, CN, $CF_3$, $N(CH_3)_3$, or $NO_2$, $R_2$ is hydrogen or an alkyl group having 1 to 4 carbon atoms such as a methyl group, an ethyl group, or an isopropyl group, and $R_3$ is hydrogen, a hydroxyl group, or a methyl group and (b) at least one cyclodextrin selected from the group consisting of α, β, γ, and δ-cyclodextrins in an aqueous phase at a mole ratio of (a):(b)=1:9−1:1 at a temperature of 50° C. to 100° C.

DESCRIPTION OF THE PREFERRED EMBODIMENTS

When the above-mentioned heat treated mixture of compounds (a) and (b) are incorporated into waving lotions containing, as a main component, a mercapto compound according to the present invention, only mercaptan causing an unpleasant odor can be selectively captured to effectively prevent vaporization of the unpleasant odor, without decreasing the desired fundamental reducing effect or power, based on thioglycolic acid, cysteine, and other mercapto compounds, of the waving lotion (i.e., the mercapto compounds are not substantially consumed by the above-mentioned heat treated mixtures).

The compounds (a) usable in the formation of the heat treated aqueous mixture are those having the above-mentioned general formulae (I) to (XX). These compounds may be used alone or in any mixture thereof. The preferable compounds are: p-hydroxy acetophenone, 1-acetyl-4-carboxy methyl benzene, 1-acetyl-4-carboxy ethyl benzene, p-diacetyl benzene, and p-nitro acetophenone included in the general formula (I), β-methyl naphthyl ketone included in the general formula (III), hinokitiol included in the general formula (IV), 2-cyclohexanone and carvone included in the general formula (X), and 2-hydroxy-1,4-naphthoquinone included in the general formula (XII).

The compounds (b) usable in the formation of the above-mentioned heat treated aqueous mixture are α-, β-, γ-, or δ-cyclodextrin, or any mixture thereof. Typical cyclodextrins are α-, β-, and γ-cyclodextrins.

The compounds (a) and (b) should be heat treated in an aqueous phase at a temperature of 50° C. to 100° C. preferably 70° C. to 90° C. at a mole ratio of (a):(b)=1:9 to 1:1, preferably 1:4 to 1:1.

When the amount of the compound (a) is less than 1 mole based on 9 moles of the compound (b) or is more than 1 mole based on 1 mole of the compound (b), the desired effect of eliminating the unpleasant mercaptan odor from the waving lotion or during the processing of the waving lotion cannot be obtained. On the other hand, when the heat treatment temperature is less than 50° C., the desired effect of eliminating the unpleasant mercaptan odor cannot be obtained.

The heat treatment of the compounds (a) and (b) can be effected in any conventional manner, desirably, while stirring, in an aqueous phase. There is no specific limitation to the heat treatment time. It is not necessary to heat for a long time. The heating time is generally 1 to 5 minutes. The solid content of the heat treated aqueous mixture can be varied in a wide range, for example, from 0.2 W/W % to 50 W/W %, desirably 1 W/W % to 10 W/W %, from the viewpoint of the operation.

The heat treated aqueous mixture of the compounds (a) and (b) may directly be incorporated into a waving lotion. The preferably solid content of the heat treated mixture in the waving lotion is 0.0002% to 40% by weight, more desirably 0.05% to 5% by weight. The use of too small an amount of the heat treated mixture of the compounds (a) and (b) does not exhibit the desired odor elimination effect, whereas the use of too large an amount of the heat treated mixture results in no substantial increase in the unpleasant mercaptan odor elimination effect.

The mechanism of the unpleasant mercaptan odor elimination of the above-mentioned heat treated aqueous mixture of the compounds (a) and (b) is not clearly understood, but it would seem that, without prejudice to the present invention, inclusion complexes are formed between the compounds (a) and (b) in the aqueous mixture during the heat treatment and these inclusion complexes do not attack thioglycolic acid, cysteine, and other mercapto compounds, but are selectively reacted with mercaptan. We believe that, since the compounds (a) having the general formulae (I) to (XX) have one or more carbonyl groups therein, the inclusion complexes with the compounds (b) are formed upon heating taking into consideration the molecular sizes and the locations of the substituted groups of the compounds (a).

The waving lotion of the present invention may contain, as a main component, any conventional mercapto compound. Examples of such mercapto compounds are thioglycolic acid, thioglycolates such as sodium thioglycolate, potassium thioglycolate, ammonium thioglycolate, monoethanol amine thioglycolate, glycerol monothioglycolate, thiolactic acid and its salts, and L-Alginine thioglycolate, cysteine, cysteine derivatives such as N-acetyl-L-cysteine, and cysteine ethylester, and salts, such as hydrochloric acid, and sulfuric acid salts, of the cysteine derivatives. These mercapto compounds may be used alone or in any mixtures thereof. Although there is no specific limitation in the content of the mercapto compounds in the waving lotion, the mercapto compounds are preferably incorporated into the waving lotion in an amount of 2% to 10% by weight, more preferably 3% to 7% by weight, based on the total weight of the waving lotion.

The waving lotion of the present invention may optionally contain any conventional ingredients used in conventional waving lotions. Examples of such conventional ingredients are hair softening agents such as ammonia, alkylol amines, and ammonium salts, oils such as liquid paraffines, squalene, fatty alcohols, triglyceride, esters, silicone oils, and lanolin, surfactants such as nonionic surfactants (e.g., polyoxyethylene alkyl ether), anionic surfactants (e.g., sodium lauryl sulfate, sodium laurate), and cationic surfactants (e.g., stearyl trimethyl ammonium chloride), sequestrants such as ethylene diamine tetra acetate (EDTA), colorants such as Guaiazulene, Quinoline yellow WS (D. & C. Yellow No. 10), Rhodamine B (D. & C. Red No. 19), perfumes, preservatives such as methyl parabene, sodium benzoate, and other agents such as water soluble polymers, cationic polymers, polypeptide, amino acids, and humectants.

The waving lotion according to the present invention may be applied to the hair in the same manner as conventional waving lotions. After waving the hair, the hair is treated with conventional neutralizers containing, as a main component, bromate such as sodium bromate, potassium bromate, hydrogen peroxide, sodium percarbonate, and sodium perborate in any conventional manner.

EXAMPLE

The present invention now will be further illustrated by, but is by no means limited to, the following examples, in which all percentages and parts are expressed on a weight basis unless otherwise specified.

EXAMPLE 1

The compounds listed in Table 1 below were incorporated into the following standard formulation to prepare waving lotions.

| Standard formulation Composition | % by weight |
| --- | --- |
| 50% Aqueous ammonium thioglycolate | 13.0 |
| Ammonium bicarbonate | 5.0 |
| Tetrasodium EDTA*[1] | 0.1 |
| Compound listed in Table 1 | see Table 1 |
| Purified water | balance |

*[1]Ethylene diamine tetraacetic acid

The waving lotions thus obtained were evaluated as follows.

1. Hair waving effect

Hair was wounded around rods and, then, was treated with the waving lotions prepared above, followed by treatment with a neutralizer.

The composition of the neutralizer was as follows:

| Components | % by weight |
|---|---|
| Sodium bromate | 5.0 |
| Disodium phosphate, dibasic | 0.1 |
| Potassium phosphate, monobasic | 0.4 |
| Sodium benzoate | 0.1 |
| Purified water | balance |

The waving effects of the waving lotions were evaluated from the formed coils. It is considered that the smaller the diameter (mm) of the resultant coil is, the larger the waving power is.

2. Odor of waving lotion

The hydrogen sulfide generated in the upper spaces of the waving lotion containers was quantitatively determined by gas chromatography (FPD). The waving lotions were allowed to stand at room temperature for 5 months.

The hydrogen sulfide contents were organoleptically evaluated as follows:

| | |
|---|---|
| 300 ppm or more: | Very strong mercaptan odor |
| 150 ppm to 300 ppm: | Strong mercaptan odor |
| 70 ppm to 150 ppm: | Weak mercaptan odor |
| 0 to 70 ppm: | No substantial mercaptan odor |

3. Reaction odor in hair

A 0.5 g amount of hair was mixed with 1.0 g of the waving lotion. The mixture was placed in a 400 ml plastic container and was allowed to stand at a temperature of 30° C. for 20 minutes. After 20 minutes, the odor was determined by means of gas chromatography and by smelling.

As is clear from Run Nos. 5 to 6 in Table 1, the mercaptan odor of the waving lotions and the reaction odor of the waving lotions in the hair were eliminated or suppressed by incorporating the heat treated mixture of p-diacetyl benzene and cyclodextrin into the waving lotions.

TABLE 1

| No. | Compound incorporated into waving lotion | Appearance of waving lotion | pH | Waving effect (mm) | Odor of waving lotion H2S (ppm) | Reaction odor in hair H2S (ppm) |
|---|---|---|---|---|---|---|
| 1 | No addition | Crystal clear | 8.1 | 13.04 | 149 | 350 |
| 2 | p-Diacetyl benzene 0.06% | Crystallization | 8.0 | 13.11 | 143 | 353 |
| 3 | β-Cyclodextrin 1.14% | Substantially transparent | 8.2 | 13.54 | 155 | 320 |
| 4 | Celdex CH-20*[1] 5.0% | Crystal clear | 8.1 | 13.35 | 165 | 360 |
| 5 | β-Cyclodextrin 1.14% + p-Diacetyl benzene 0.06%*[2] | Substantially transparent | 8.2 | 12.06 | 25 | 105 |
| 6 | Celdex CH-20*[1] 5.0% + p-Diacetyl benzene 0.06%*[2] | Crystal clear | 8.2 | 11.89 | 20 | 93 |

*[1]About 20% aqueous cyclodextrins (mixture) manufactured by NIHON SHOKUHIN KAKO CO., LTD.
*[2]The mixture was heat treated at a temperature of 85° C. for 5 minutes, while stirring, after adding cyclodextrin and p-diacetyl benzene to water.

EXAMPLE 2

The effects of various compounds represented by the general formulae (I) to (XX) on the elimination of the unpleasant mercaptan odor were evaluated in the same manner as in Example 1. The heat treated mixtures were prepared in the same manner as in Example 1.

The results are shown in Table 2.

As is clear from the results shown in Table 2, the compounds having $R_1$ of electron attractive groups, as in Nos. 6 to 10 and 12, in the general formulae (I) to (XX) were effective, whereas the compounds having $R_1$ of electron donating groups as in Nos. 2 to 4 were not effective as compared with the compounds having $R_1$ of hydrogen. As $R_2$ in the general formulae, hydrogen was effective as shown in No. 11, and the effect was decreased in the cases of $CH_3$ and $C_2H_5$ in this order (see Nos. 5 and 13). In the case of $R_2$ being $C_5H_{11}$, the effect was remarkably decreased as shown in No. 14 and no substantial advantage was obtained by the incorporation thereof into waving lotions. In addition to the benzene ring as in Nos. 2 to 14, a naphthalene ring as in No. 15 and cyclic conjugated ketones as in Nos. 16 to 19 were effective as a mother nucleus.

TABLE 2

| No. | Compound General formula | $R_1$ | $R_2$ | $R_3$ | Incorporated amount (%) | β-Cyclodextrin (%) | pH | Waving effect (mm) | Odor of waving lotion H2S (ppm) | Reaction odor in hair H2S (ppm) |
|---|---|---|---|---|---|---|---|---|---|---|
| 1 | — | — | — | — | — | — | 8.0 | 12.1 | 155 | 380 |
| 2 | | OH | CH3 | — | 0.1 | 1.14 | 8.0 | 11.9 | 143 | 350 |
| 3 | | C2H5 | CH3 | — | " | " | 7.9 | 11.8 | 115 | 348 |
| 4 | | CH3 | CH3 | — | " | " | 7.8 | 12.9 | 93 | 330 |
| 5 | | H | CH3 | — | " | " | 7.8 | 12.1 | 30 | 150 |
| 6 | | Cl | CH3 | — | " | " | 7.8 | 12.2 | 18 | 126 |
| 7 | COR2 | OCOCH3 | CH3 | — | " | " | 7.8 | 12.0 | 15 | 103 |
| 8 | | OCOC2H5 | CH3 | — | " | " | 7.8 | 12.5 | 14 | 115 |
| 9 | | COCH3 | CH3 | — | " | " | 7.8 | 11.9 | 11 | 96 |
| 10 | R1 | NO2 | CH3 | — | " | " | 7.9 | 12.0 | 15 | 110 |
| 11 | | H | H | — | " | " | 7.8 | 12.4 | 13 | 117 |
| 12 | | NO2 | H | — | " | " | 7.8 | 12.1 | 14 | 90 |

TABLE 2-continued

| No. | General formula | R₁ | R₂ | R₃ | Incorporated amount (%) | β-Cyclodextrin (%) | pH | Waving effect (mm) | Odor of waving lotion H₂S (ppm) | Reaction odor in hair H₂S (ppm) |
|---|---|---|---|---|---|---|---|---|---|---|
| 13 | | H | C₂H₅ | — | " | " | 7.8 | 11.8 | 36 | 121 |
| 14 | | H | C₅H₁₁ | — | " | " | 7.9 | 11.9 | 73 | 300 |
| 15 | 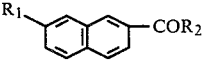 | | H | CH₃ | — | " | " | 7.8 | 12.2 | 20 | 130 |
| 16 | 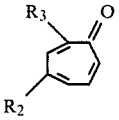 | | — | C₃H₇ | OH | " | " | 7.8 | 12.0 | 25 | 127 |
| 17 | 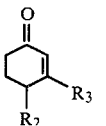 | | — | H | H | " | " | 7.9 | 12.1 | 30 | 131 |
| 18 | | | — | C₃H₆ | CH₃ | " | " | 7.8 | 12.3 | 35 | 135 |
| 19 | 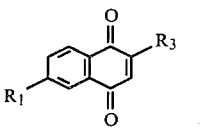 | | H | — | OH | " | " | 7.7 | 12.5 | 32 | 123 |

EXAMPLE 3

A waving lotion having the following composition was prepared.

| Composition | % by weight |
|---|---|
| 50% Aqueous ammonium thioglycolate monoethanolamine | 12.5 |
| 28% Aqueous ammonia | 1.0 |
| Tetrasodium EDTA | 2.0 |
| Heat treated mixture of p-diacetyl benzene and Celdex CH20*¹ | 0.1 |
| Purified water | 30.0 |
|  | 54.2 |

*¹Obtained by adding 0.06% of p-diacetyl benzene and 5.00% of Celdex CH20 to 24.94% of purified water and, then, heating the mixture at a temperature of 85° C. to 90° C. for 5 minutes while stirring, followed by cooling to room temperature.

The above components were mixed at room temperature to prepare the waving lotion.

A neutralizer having the following composition was prepared by mixing the components at room temperature.

| Composition | % by weight |
|---|---|
| Sodium bromate | 5.0 |
| Buffer (i.e., disodium phosphate) | q.s. |
| Preservative (i.e., sodium benzoate) | q.s. |
| Purified water | balance |

According to a conventional processing method of permanent waving lotion, the waving lotion was first applied in an amount of 80 ml/person and, then, the neutralizer was then applied in an amount of 100 ml/person.

The mercaptan odor was very weak when the cap was taken out from the container of the waving lotion and also when the waving lotion was applied. Thus, the use of the heat treated mixture was very effective for eliminating the unpleasant mercaptan odor. After the application of the neutralizer, good waves were formed to have been formed when rods were removed. The resultant permanent wave was elastic and bright.

EXAMPLE 4

A waving lotion having the following composition was prepared:

| Composition | % by weight |
|---|---|
| 50% Aqueous ammonium thioglycolate | 13.0 |
| Ammonium bicarbonate | 5.0 |
| Trisodium EDTA | 0.1 |
| Cetyl alcohol | 0.5 |
| Polyoxyethylene oleyl ether (E.O. = 20 mole) | 0.1 |
| Sodium lauryl sulfate | 0.05 |
| Heat treated mixture of methyl-β-naphtyl ketone and β-cyclodextrin*¹ | 40.0 |
| Purified water | 41.25 |

*¹Obtained from 0.03% of methyl-β-naphtyl ketone, 1.00% of β-cyclodextrin and 38.97% of purified water in the same manner as in Example 3.

The waving lotion was prepared as follows. Cetyl alcohol, polyoxyethylene oleyl ether (E.O.=20 mole), and sodium lauryl sulfate were melted upon heating and, then, mixed heated water having a temperature of about 70° C. The resultant mixture was cooled while gradually stirring to obtain viscous white gel. The other starting materials were incorporated into the gel and the heat treated mixture. The mixture was gradually stirred at room temperature to obtain a viscous translucent white waving agent.

The cold waving was carried out by using the above-prepared waving lotion and the neutralizer prepared in Example 3. As a result, no substantial mercaptan odor was detected during the application thereof and the ammonia odor was very weak. The wave thus obtained was bright and elastic. Only a weak ammonia odor was detected from the mouth of the waving lotion container. No substantial mercaptan odor was detected.

EXAMPLE 5

A waving lotion having the following composition was prepared in the same manner as in Example 3.

| Composition | % by weight |
| --- | --- |
| 50% Aqueous ammonium thioglycolate | 13.0 |
| Monoethanolamine | 0.5 |
| Ammonium bicarbonate | 4.5 |
| Trisodium EDTA | 0.2 |
| Heat treated mixture of hinokitiol and Celdex CH-20*[1] | 50.0 |
| Polyoxyethylene oleyl ether (E.O. = 15 mole) | 0.5 |
| Perfume | 0.1 |
| Colorant | q.s. |
| Purified water | balance |

*[1]Obtained from 0.28% of hinokitiol, 40.0% of Celdex CH-20 and 9.72% of purified water in the same manner as in Example 3.

A mercaptan odor and an ammonia odor during the application of the waving lotion to the hair as well as the remaining odor of the hair were not substantially detected. The elastic wave was formed. No substantial odor was detected from the month of the container.

EXAMPLE 6

A waving lotion having the following composition was prepared in the same manner as in Example 4.

| Compostion | % by weight |
| --- | --- |
| L-Cystine | 5.0 |
| Monoethanolamine | 3.0 |
| Tetrasodium EDTA | 0.5 |
| Cetyl alcohol | 0.7 |
| Polyoxyethylene cetyl ether (E.O. = 10 mole) | 0.1 |
| 60% Aqueous stearyl trimethyl ammonium chloride | 0.2 |
| Heat treated mixture of l-carvone and Celdex CH-20*[1] | 30.0 |
| Purified water | 60.5 |

*[1]Obtained from 0.1% of l-carvone, 4.0% of Celdex CH20, and 25.9% of purifed water in the same manner as in Example 3.

The gel was obtained from cetyl alcohol, polyoxyethylene cetyl ether (E.O.=10 mole), and stearyl trimethyl ammonium chloride in the same manner as in Example 4. From this gel, the waving lotion was prepared in the same manner as in Example 4.

A mercaptan odor and an ammonia odor during the application of the waving lotion to the hair as well as the remaining mercaptan odor of the hair were not substantially detected and only an l-carvone odor was slightly smelt. The elasticity of the hair thus obtained was less than the elasticity obtained in Examples 3 and 4, but a desirable soft wave was obtained. No mercaptan odor was detected in the waving lotion.

EXAMPLE 7

A waving lotion having the following composition was prepared in the same manner as in Example 3.

| Composition | % by weight |
| --- | --- |
| 40% aqueous monoethanolamine thioglycolate | 10.0 |
| N—Acetyl-L-cystine | 3.0 |
| Tetrasodium EDTA | 0.5 |
| Heat-treated mixture of p-nitro acetophenone, methyl-β-naphtyl ketone, and Celdex CH-20*[1] | 60.0 |
| Ammonium bicarbonate | 4.0 |
| Monoethanolamine | 1.0 |
| Polyoxyethylene oleyl ether (E.O. = 15 mole) | 0.5 |
| Perfume | 0.2 |
| Glycerine | 2.0 |
| Colorant | q.s. |
| Purified water | balance |

*[1]Obtained from 0.15% of p nitro acetophenon, 0.03% of methyl-β-naphthayl ketone, 10.0% of Celdex CH-20, and 49.82% of purified water in the same manner as in Example 3.

No substantial mercaptan odor, except for an ammonia odor, was detected from the mouth of the waving lotion container. The reaction odor in the hair was weak and a bright and elastic wave was formed.

EXAMPLE 8

A waving lotion having the following composition was prepared in the same manner as in Example 3.

| Composition | % by weight |
| --- | --- |
| 50% Aqueous ammonium thioglycolate | 12.5 |
| Monoethanolamine | 1.0 |
| 28% Aqueous ammonia | 2.0 |
| Tetrasodium EDTA | 0.1 |
| Cetyl alcohol | 0.5 |
| Polyoxyethylene cetyl ether (E.O. = 20 mole) | 0.1 |
| 60% Aqueous stearyl trimethyl ammonium chloride | 0.15 |
| Heat treated mixture of p-diacetyl benzene and Celdex CH30*[1] | 50.0 |
| Purified water | 83.6 |

*[1]Obtained from 0.05% of p-diacetyl benzene, 10.0% of Celdex CH30H (i.e., about 20% aqueous solution of cyclodextrins manufactured by NIHON SHOKUHIN KAKO CO., LTD.), and 39.95% of purified water in the same manner as in Example 3.

The cold waving was carried out by using the above-prepared waving lotion and the neutralizer prepared in Example 3. No substantial mercaptan odor was detected during the application of the waving lotion to the hair and an elastic wave was obtained. No substantial mercaptan odor was detected in the waving lotion.

We claim:

1. In an aqueous waving lotion for cold waving comprising (i) a mercapto compound, the improvement wherein such composition further contains (ii) an aqueous mixture obtained by heating (a) at least one compound selected from the group consisting of the compounds having the general formulae (I) to (XX),

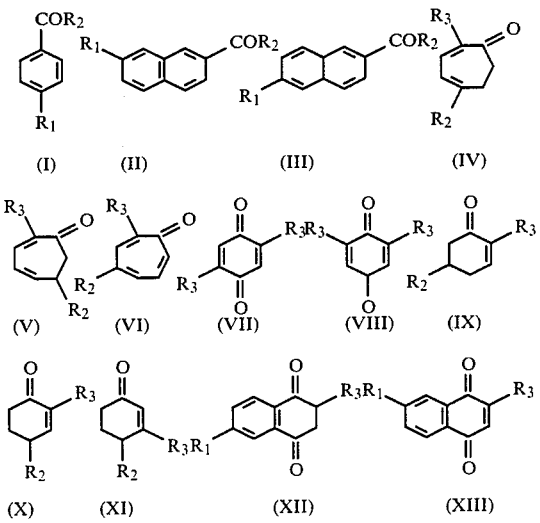

-continued

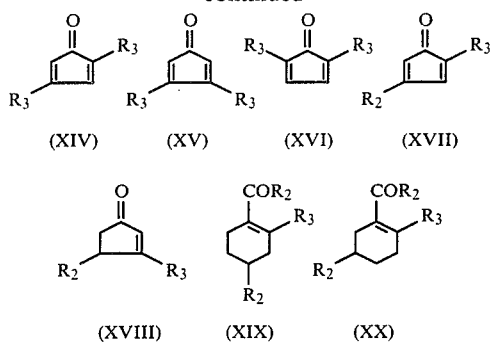

(XIV) (XV) (XVI) (XVII) (XVIII) (XIX) (XX)

wherein $R_1$ is hydrogen, $COCH_3$, $COC_2H_5$, $COC_3H_7$, $OCOCH_3$, $OCOC_2H_5$, $OCOC_3H_7$, Cl, Br, I, $SCOCH_3$, SCN, CN, $CF_3$, $N(CH_3)_3$, or $NO_2$, $R_2$ is hydrogen or an alkyl group having 1 to 4 carbon atoms, and $R_3$ is hydrogen, a hydroxyl group, or a methyl group, and (b) at least one cyclodextrin selected from the group consisting of α-, β-, γ-, and δ-cyclodextrins in an aqueous phase at a mole ratio of (a):(b)=1:9 to 1:1 at a temperature of 50° C. to 100° C., the solid content of the aqueous mixture (ii) in the waving lotion being 0.0002% to 40% by weight.

2. A waving lotion as claimed in claim 1, wherein the content of the mercapto compound in the waving lotion is 2% to 10% by weight.

3. A waving lotion as claimed in claim 1, wherein the mercapto compound (i) is at least one compound selected from the group consisting of thioglycolic acid, sodium thioglycolate, potassium thioglycolate, ammonium thioglycolate, L-Alginine thioglycolate, monoethanolamine thioglycolate, glycerol monothioglycolate, thiolactic acid, cysteine, N-acetyl-L-cycsteine, cysteine ethyl ester, and hydrochloric acid and sulfuric acid salts of N-acetyl-L-cysteine and cysteine ethyl ester.

4. A waving lotion as claimed in claim 1, wherein the compound (a) is at least one compound selected from the group consisting of p-hydroxy acetophenone, 1-acetyl-4-carboxy methyl benzene, 1-acetyl-4-carboxy ethyl benzene, p-diacetyl benzene, and p-nitro acetophenone included in the general formula (I), β-methyl naphthyl ketone included in the general formula (III), hinokitiol included in the general formula (IV), 2-cyclohexanone and carvone included in the general formula (X), and 2-hydroxy-1,4-naphthoquinone included in the general formula (XII).

* * * * *